United States Patent [19]
Nevermann

[11] Patent Number: 5,620,655
[45] Date of Patent: Apr. 15, 1997

[54] COMPOSITION AND METHOD FOR KILLING PARASITES AND INVASIVE DURABLE FORMS OF SAID PARASITES

[75] Inventor: Eugen Nevermann, Hamburg, Germany

[73] Assignee: Menno-Chemie-Vertrieb GmbH, Norderstedt, Germany

[21] Appl. No.: 501,075

[22] PCT Filed: Feb. 10, 1994

[86] PCT No.: PCT/EP94/00382

§ 371 Date: Aug. 4, 1995

§ 102(e) Date: Aug. 4, 1995

[87] PCT Pub. No.: WO94/17661

PCT Pub. Date: Aug. 18, 1994

[30] Foreign Application Priority Data

| Feb. 11, 1993 | [DE] | Germany | 43 04 541.3 |
| Feb. 24, 1993 | [DE] | Germany | 43 06 336.5 |
| May 5, 1993 | [DE] | Germany | 43 17 083.8 |

[51] Int. Cl.⁶ .......................... A01N 27/00; A01N 25/00; A61L 2/16
[52] U.S. Cl. ................................ 422/28; 424/405
[58] Field of Search ................ 422/28, 40; 424/405; 514/919

[56] References Cited

U.S. PATENT DOCUMENTS

| 3,991,124 | 11/1976 | Schellenbaum | 106/18.34 X |
| 4,000,301 | 12/1976 | Walworth | 514/407 |
| 4,558,139 | 12/1985 | Hagenmaier et al. | 549/271 |

*Primary Examiner*—Robert J. Warden
*Assistant Examiner*—E. Leigh Dawson
*Attorney, Agent, or Firm*—Michael J. Striker

[57] ABSTRACT

A disinfectant composition for killing parasites and invasive durable forms of parasites is made from a disinfection agent concentrate or mixture containing one or more phenols, preferably 4-chloro-3-methylphenol, in combination with one or more keratolytically acting organic acids, preferably formic acid, salicylic acid, and/or thioglycolic acid, as active disinfectant ingredients; a solvent ingredient including one or more ethylene glycol dialkyl ether of the formula $H_3CO(CH_2—CH_2—O)_nCH_3$ wherein n=1 to 8 and, optionally, alcohols having 2 to 4 carbon atoms and polyethylene or polypropylene glycol; one or more anionic surfactants which can be sodium or potassium alkyl sulfonates or sulfates, having independently, primary or secondary chains of from 8 to 18 carbon atoms with or without n-alkyl-aryl sulfonates or their potassium or sodium salts having n-alkyl groups with from 10 to 13 carbon atoms; and, optionally, nonylphenol polyglycol ether ethoxylated with from 2 to 18 Mol of ethylene oxide.

19 Claims, 3 Drawing Sheets

COMPOSITION AND METHOD FOR KILLING PARASITES AND INVASIVE DURABLE FORMS OF SAID PARASITES

BACKGROUND OF THE INVENTION

The invention relates to a disinfection agent based on a mixture for fighting parasitoses and for killing invasive durable forms.

In intensive livestock keeping, infestation by parasites represents an undiminished grave danger to breeding. Despite the large variety of possible systemic treatments of parasitoses, the use of medications remains without lasting effect unless hygiene (cleaning) in the stall is supplemented with special disinfection methods.

Poultry, hog, and cattle raising and breeding suffer from the fact that these types of animals are infested with coccidia and ascarides. Despite the feeding of anti-helminthic and anti-coccidial agents, animal infections occur repeatedly, since the animals excrete in their feces the highly resistant durable forms (ascarides eggs and coccidia oocysts) of parasites, which are invasive and can reenter the animal's body by ingestion.

These parasites act on the intestinal tract and cause extensive lesions, which result in the atrophy or death of animals.

Disinfection agents with particular active-ingredient additives are used to combat this danger. These special additives are mostly chlorinated solvents or carbon disulfide in an emulsified form. Dual-component preparations that split off carbon disulfide are also in use.

The task of the aforementioned solvent is to penetrate the very tough membranes of parasitic durable forms and thus to enable the entry into the interior of the parasitic durable forms, which makes it possible to damage the parasites irreversibly.

The range of application of the present invention consequently lies in the area of mass livestock keeping, but not in household cleaning or medical use. Therefore the subject of the application does not touch upon any bactericidal action; the parasiticidal action is the subject of the invention. The bactericidal action, which is likewise present, of the active ingredient combination is an inevitable side effect.

Ascarides belong to the genus of roundworms, but coccidia belong to the telosporides, which are parasitic protozoa (protozoa with a mobile initial stage). Both ascarides and coccidia are microorganisms, which due to their size, morphology, and way of life, as well as their mechanism of reproduction, have no zoological relation whatsoever to microbes and bacteria. Ascarides eggs, e.g. of the ascaris suum type, have an eggshell comprising three layers. In particular, the middle layer of chitin-like substances and the vitelline membrane, which contacts its inside, can only be penetrated with difficulty. The agents used up to now against ascarides eggs therefore contain organic solvents, chlorinated hydrocarbons such as carbon tetrachloride and tetrachloroethylene or carbon disulfide so that the phenolic active ingredients can reach through the eggshell into the inside.

A particular disadvantage of this method, which corresponds to the prior art, is that the solvents necessary for the effectiveness of the disinfection preparations are classified as highly questionable from an ecological and toxicological standpoint. So the commercially available disinfection preparations with a proven parasiticidal action contain between 5 and 20% carbon disulfide or between 10 and 50% chlorinated hydrocarbons (tetrachloroethylene, chloroform).

Carbon disulfide is highly flammable, explosive, and poisonous. Halogenated solvents in general are particularly long-lived environmental poisons.

SUMMARY OF THE INVENTION

The object of the present invention is to overcome the grave disadvantages of parasiticidal disinfection agents which correspond to the prior art.

It is also an object of the present invention to prevent use of substances which represent an indirect or direct danger to the environment.

According to the invention the a disinfection agent is based on a concentrated mixture or disinfection agent concentrate for fighting parasitoses and killing of parasitic, invasive durable forms. The above-described objects are attained when that concentrated mixture or disinfection agent concentrate comprises:

a) one or more phenols—preferably 4-chloro-3-methylphenol —in combination with keratolytically acting organic acids, preferably formic acid, salicylic acid, and thioglycolic acid, individually or in a mixture with one another, as the active disinfection ingredient, b) ethylene glycol dialkyl ether of the general formula $H_3CO(CH_2-CH_2-O)_nCH_3$ (n=1–8) or a mixture of various chain lengths of this ether, c) sodium or potassium salts of alkyl sulfonates or alkyl sulfates with primary or secondary chains of $C_8$–$C_{18}$ length or a mixture thereof as anionic surfactants.

Surprisingly it has now been found that toxic solvents can be eliminated from parasiticidal disinfection agents if a combination of phenols and this kind of organic acids is used as the active ingredient; this combination has keratolytic properties. These acids preferably include salicylic acid, thioglycolic acid, and formic acid.

The disinfection agents according to the invention are characterized in that they contain one or more phenolic active disinfection ingredients, such as, phenol, substituted phenols, cresols and halogenated cresols, in particular 2-methylphenol, 3-methylphenol, 4-methylphenol, 4-ethylphenol, 2,4-dimethylphenol, 2,5-dimethylphenol, 3,4-dimethylphenol, 2,6-dimethylphenol, 4-n-propylphenol, 4-n-butylphenol, 4-n-amylphenol, 4-n-hexylphenol, thymol, o-cyclohexyl-p-chlorophenol, o-n-amyl-p-chorophenol, o-n-hexyl-p-chlorophenol, p-chloro-m-cresol, 4-tert.-butyl-2,6-dichlorophenol, 6-tert.-butyl-4-chloro-m-cresol, 4-ethyl-4-chlorophenol, 4-chloro-3,5-xylenol, 2,4-dichloro-3,5-xylenol, p-phenyl phenol, o-phenyl phenol, 2-benzylphenol, p-chloro-o-phenyl phenol, benzyl-4-chloro-m-cresol, and 4-chlorobenzyl-dichloro-m-cresol, but preferably p-chloro-m-cresol. According to the invention, phenol derivatives and organic acids with keratolytic properties, preferably salicylic acid, thioglycolic acid, and formic acid, or with a mixture of these acids are used as the active disinfectant ingredient. Anionic surfactants of the type of n-alkyl($C_{10}$–$C_{13}$)-aryl sulfonates and/or alkyl sulfonates or alkyl sulfates as sodium or potassium salts, with primary or secondary chains ($C_8$–$C_{18}$) in length, or a mixture thereof, are used in the disinfection agents according to the invention as emulsifiers for the active ingredient combination as well as for spreading the substances onto the surfaces to be disinfected. Examples of n-alkyl($C_{10}$–$C_{13}$)-aryl sulfonates are in particular mixtures of n-alkyl($C_{10}$–$C_{13}$)-benzene sulfonates, whose alkyl radical has 10–13 carbon atoms. Examples of alkyl radicals with 10–13 carbon atoms are the n-decyl, n-undecyl, n-dodecyl, and n-tridecyl groups. Primary or secondary chains of the ($C_8$–$C_{18}$) length are illustrated by the following groups: n-octyl, 2-octyl, n-nonyl, 2-nonyl, n-decyl, 2-decyl, n-undecyl, 2-undecyl, n-dodecyl, 2-dodecyl, n-tridecyl, 2-tridecyl, n-tetradecyl, 2-tetradecyl, n-pentadecyl, 2-pentadecyl, n-hexadecyl , 2-hexadecyl, n-heptadecyl, 2-heptadecyl, n-octadecyl, and 2-octadecyl groups. According to the invention, ethylene glycol dialkyl ether of the general formula $H_3CO(CH_2-CH_2-O)_nCH_3$ (n=1–8), glycols, and alcohols of the 2–4 chain length, as well as their isomeric forms, are used individually or in mixture as a solvent. The object of the solvents is not to directly contribute to the parasiticidal action —comparable to the tetrachloroethylene or carbon disulfide, but to serve as necessary adjuvants for the production of a disinfection agent concentrate (solution of phenol derivatives and acids). The active ingredient mixture according to the invention can contain nonylphenol polyglycol ether (2–18 EO) to improve the spreading behavior on surfaces, and can furthermore contain up to 30% water.

The disinfection agents according to the invention produce better results that those demanded by the testing guidelines of the DVG (German Society of Veterinary Medicine) for chemical disinfection agents. Furthermore, to test the effectiveness against coccidia oocysts, in addition to the DVG method, which represents in a practical manner a qualitative assessment of the effectiveness, a new test method was used, which supplements the DVG method by means of a quantitative process. Within this testing process, which de facto includes a distinct intensification of test conditions, the disinfection agents according to the invention in turn showed their superiority over the disinfection agents, which correspond to the prior art.

Surprisingly it has in fact been found that the keratolytically acting acids according to the invention can also penetrate the shells of ascarides eggs. It was especially unexpected that these acids would not be held back by the above mentioned chitin-like layer.

Keratolytic action means that keratins are broken down. Keratins, however, are proteins, in contrast to the chitin of ascarides eggs, which is a polysaccharide. Due to the different structures of proteins and polysaccharides, it was not expected that the keratolytically active acids could penetrate a chitin layer, since proteins have amide bonds, which can easily be separated hydrolytically, while polysaccharides, primarily chitin, are essentially harder to break down hydrolytically. But even overcoming a barrier in the form of a chitin layer in another manner, such as by hydrolysis, can only be achieved with difficulty. Thus, in a way that is known, the chitin armor of insects is particularly resistant. It is therefore completely surprising when a mixture containing keratolytically acting acids can be used against the highly resistant durable forms of parasites without the addition of OE-organic solvents.

The weight ratio of the at least one keratolytically acting organic acid to the at least one phenol is preferably between 1:9 and 9:1 while from 25 to 50% by weight (based on a total weight of the concentrate) of a total amount of both the at least one phenol and the at least one organic acid is advantageously present in the disinfection agent concentrate.

In a preferred embodiment of the disinfection agent concentrate the solvent ingredient also includes one or more alcohols having from 2 to 4 carbon atoms and the amount of solvent ingredient in the disinfection agent concentrate amounts to between 15 and 60% by weight of the concentrate. The solvent ingredient can also include from 10 to 50% by weight of ethylene glycol or propylene glycol based on a total amount of the solvent ingredient present.

The anionic surfactant ingredient is advantageously present in the disinfection agent in an amount of from 5 to 30% by weight based on a total weight of the disinfection agent concentrate and includes n-alkyl-aryl sulfonates or their potassium or sodium salts with alkyl groups having from 10 to 13 carbon atoms. In other embodiments the disinfection agent can also include from 0.2 to 2% by weight (based on the total weight of the disinfection agent concentrate) of a nonionic surfactant consisting of nonylphenol polyglycol ether ethoxylated with from 2 to 18 Mol of ethylene oxide.

An area or stall in which an animal is kept is disinfected using a disinfectant composition made from the above-described disinfection agent concentrate by diluting with water. This improved disinfection method according to the invention protects the animal from invasive durable forms of parasites, such as ascarides and coccidia, as well the parasites themselves.

In some embodiments the disinfectant composition can comprise 0.5 to 10 percent by weight of the disinfection agent concentrate in water.

Ascarides and ascarides eggs of the ascaris suum type are used by the German Society of Veterinary Medicine (DVG) according to guidelines for the testing of chemical disinfection agents (copy enclosed) for the evaluation of parasiticidal action. To attain an effectiveness certificate, the reliable killing of both types within a certain space of time is stipulated. This is equally true for coccidia and killing their durable forms, such as coccidia oocysts of the Eimeria tenella type. Both types of microorganisms mentioned, in particular their durable forms (eggs or oocysts) are particularly hard to kill.

The examples shown below illustrate the invention but should not be considered as limiting the scope of any of the appended claims.

The numbers after the components mentioned, which occur in the examples, indicate the parts by weight of the components.

EXAMPLES

EXAMPLE 1

| | |
|---|---|
| secondary alkyl ($C_8$–$C_{18}$) sulfonate-Na | 10.0 |
| ethylene glycol dialkyl ether | 15.0 |
| ethylene glycol | 10.0 |
| propanol-2 | 10.0 |
| 4-chloro-3-methylphenol | 20.0 |
| formic acid | 5.0 |
| thioglycolic acid | 5.0 |
| water (deionized) | 25.0 |

EXAMPLE 2

| | |
|---|---|
| alkyl-aryl sulfonate-Na | 4.2 |
| dodecyl sulfate-Na | 5.0 |
| nonylphenol polyglycol ether | 0.8 |
| ethylene glycol dialkyl ether | 35.0 |
| 4-chloro-3-methylphenol | 25.0 |
| salicylic acid | 4.0 |
| formic acid | 6.0 |
| water (deionized) | 20.0 |

EXAMPLE 3

| | |
|---|---|
| secondary alkyl (C$_8$–C$_{18}$) sulfonate-Na | 6.0 |
| dodecyl sulfate-Na | 3.0 |
| ethylene glycol dialkyl ether | 20.0 |
| ethylene glycol | 20.0 |
| 4-chloro-3-methylphenol | 25.0 |
| salicylic acid | 8.0 |
| water (deionized) | |

The results of the effectiveness tests of the exemplary formulations on the parasitic durable forms *Ascaris suum* and *Eimeria tenella* according to the DVG method and, in the event of coccidia oocysts, additionally with a broadened test method are shown in the following.

EXAMPLE 4

Test of Effectiveness of Exemplary Compositions against *Ascaris suum*.

The events described below were obtained by using the DVG test process for testing chemical disinfection agents. According to the guidelines, 90% of the ascarides eggs must be killed in order to declare a preparation as effective. The effectiveness tests were done both by the suspension test and by the germ carrier test.

More than 95% of the untreated controls embryonized.

| Disinfection agent according to Example 1) | use concentration: 5% |
|---|---|
| Action time (min.) | number of embryonized worm eggs |
| 2 | 1 |
| 5 | 0 |
| 10 | 0 |
| 20 | 0 |
| Disinfection agent according to Example 2) | use concentration: 5% |
| Action time (min.) | number of embryonized worm eggs |
| 2 | 0 |
| 5 | 0 |
| 10 | 0 |
| 20 | 0 |
| Disinfection agent according to Example 3) | use concentration: 5% |
| Action time (min.) | number of embryonized worm eggs |
| 2 | 0 |
| 5 | 0 |
| 10 | 0 |
| 20 | 0 |

EXAMPLE 5

Test of effectiveness against coccidia oocysts

According to DVG guidelines, coccidia oocysts must be inactivated by a disinfection agent within an action time of 5 minutes in such a way that they can no longer lead to infections in the animal body. Baby chickens are inoculated with 200,000 disinfected oocysts and after 8 days the following parameters are —purely qualitatively—recorded: macroscopic evaluation of intestines with regard to coccidiosis lesions and developmental forms of *Eimeria tenella* by means of mucous membrane smears. As a comparison and reference quantity relative to the disinfection agent to be tested, a 6% solution of ammonium hydroxide, with which an equal number of oocysts is treated and then a comparison group of chicks is inoculated, is used.

In this above described experimental procedure, the disinfection agents of Examples 1–3 achieved the required evaluation to be called effective.

Quantitative Test of effectiveness of Exemplary Compositions against Coccidia Oocysts It has long been known that even inoculations with only a single oocyst cause detectable infections in approximately 50% of animals. Inoculations with two oocysts regularly lead to infections. With an inoculation dose of 200,000 oocysts, a 99,999% disinfection result would have to be classified as unsatisfactory according to guidelines. Because of the range of fluctuation of the results (several groups of chicks) in the DVG test and the qualitative evaluation, such precise data with regard to relevant statistical parameters are entirely unattainable. That is why the disinfection agents according to the invention were additionally subjected to a recently available quantitative testing process. The process is based on the observation that with inoculation dosages of 20,000 and up, fewer oocysts are produced in the animal body relative to the inoculation dosage than when lesser dosages are administered (crowding effect). For inoculation dosages of fewer than 2,000 oocysts, a reproducible, regular, linear ratio arises between the value of the natural logarithm of the inoculation dosage and the value of the decadic logarithm of oocyst production in the animal's body (OpG=oocysts/g cecum content).

By regression analysis, the calibration function of the straight lines and precise, statistical parameters are obtained, which unequivocally determine the quality and confidence level of the respective animal test.

The infectiousness of an inoculum of unknown magnitude can consequently be calculated comparatively precisely from the number of oocysts produced (number of oocysts per g in the cecum).

Unlike the DVG method, with this process, no effectiveness is required for the disinfection agent after 5 minutes' action time; instead, in reliance on practice with stall infection, a killing rate of >90% after 60 minutes' action time is seen as sufficient proof of effectiveness. Here too, a 6% solution of ammonium hydroxide is used as a reference quantity for comparison with the disinfection agent to be tested.

The effectiveness of Examples 1–3 according to the invention, at a use concentration of 5% in tap water is shown as follows:

Example 1): Killing rate: 96.7%
Example 2): Killing rate: 99.4%
Example 3): Killing rate: 98.9%

For comparison, conventional preparations for stall infection, which correspond to the prior art and are based on carbon disulfide, chloroform, and tetrachloroethylene were tested. The results in the quantitative effectiveness test ranged only between killing rates of 55.2% and 837% which is a demonstration of the excellent performance of the disinfection agents according to the invention.

BRIEF DESCRIPTION OF THE DRAWING

The results of the quantitative testing of the above-described examples of the disinfection agents according to the invention are shown in the following drawing in which.

Figure 1:
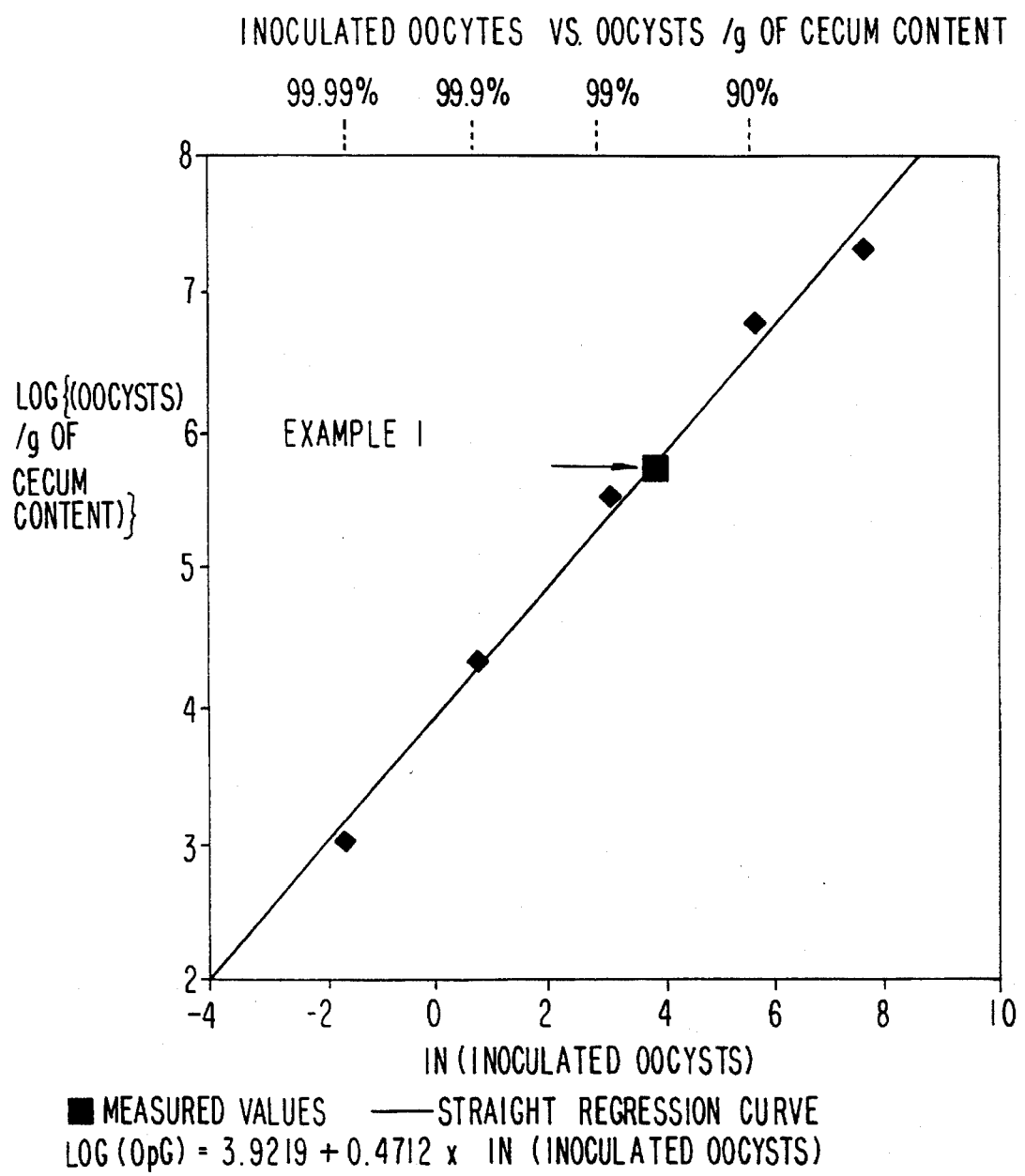
FIG. 1 is a graphical illustration showing the measured relationship between log (oocysts/g of cecum content) versus IN(innoculated oocysts) as well as the theoretical regression line obtained in a quantitative test of the disinfecting agent of example 1.
Figure 2:
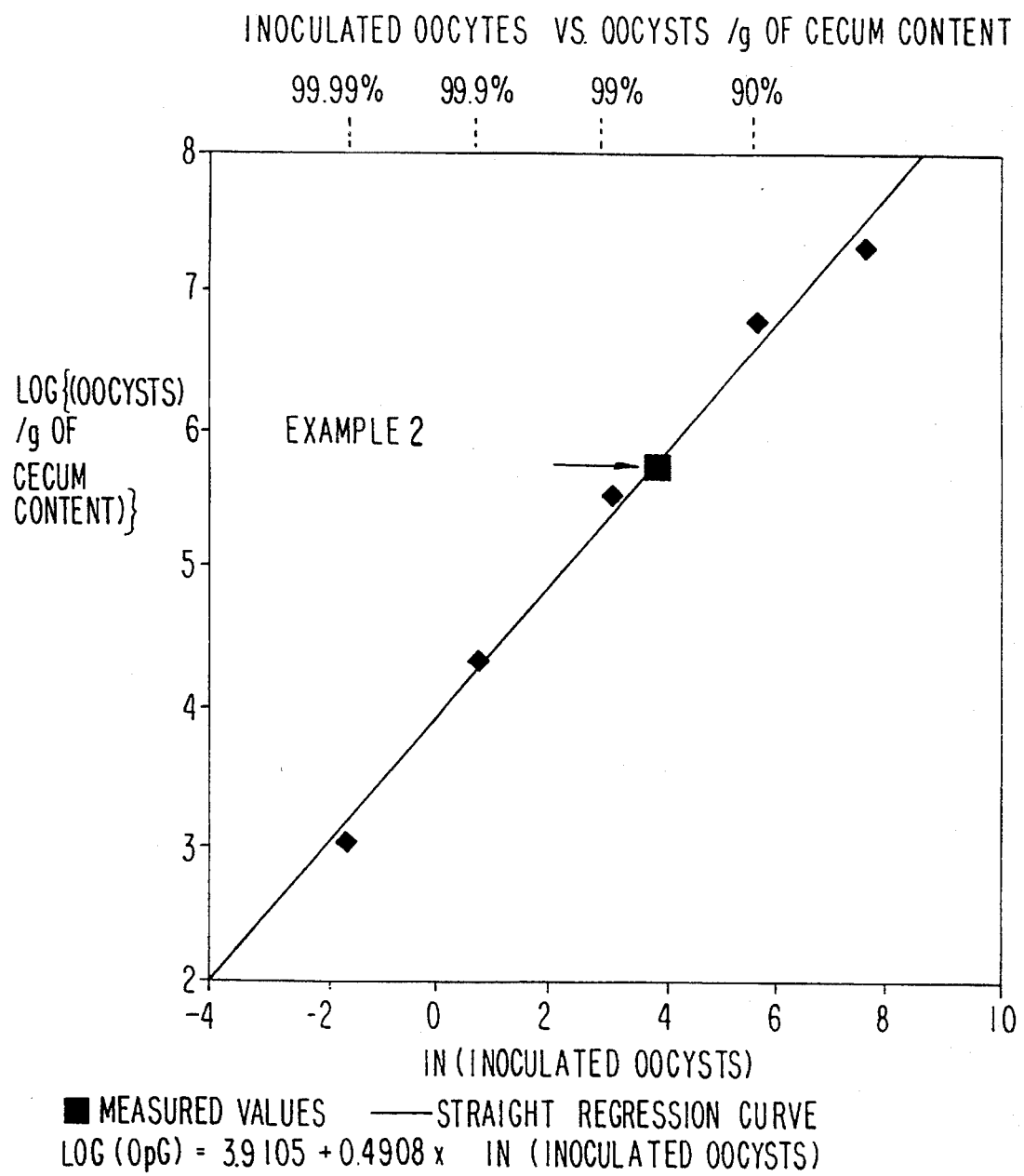
FIG. 2 is a graphical illustration showing the measured relationship between log (oocysts/g of cecum content) versus IN(innoculated oocysts) as well as the theoretical regression line obtained in a quantitative test of the disinfecting agent of example 2.
Figure 3:
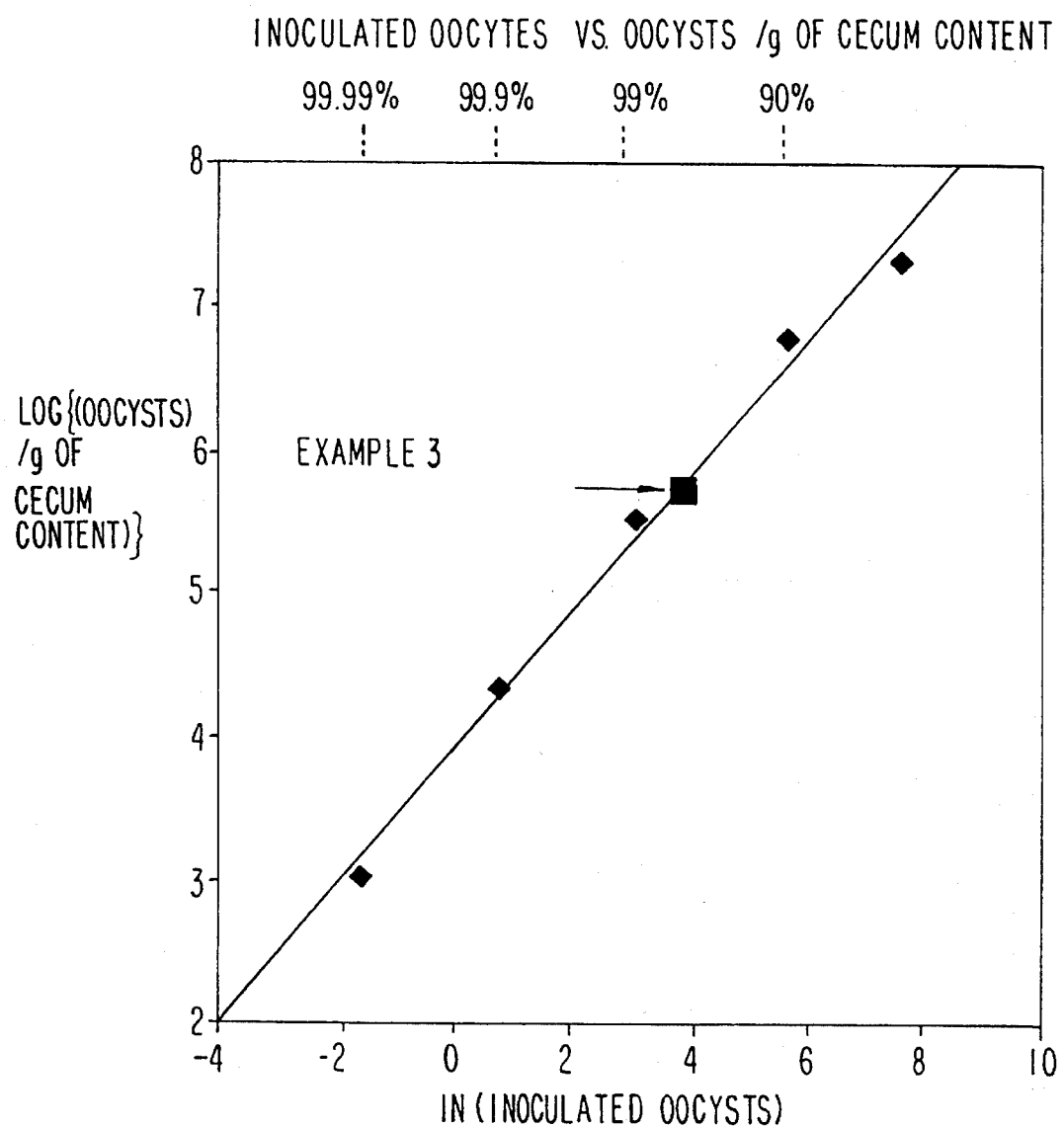
FIG. 3 is a graphical illustration showing the measured relationship between log (oocysts/g of cecum content) versus IN(innoculated oocysts) as well as the theoretical regression line obtained in a quantitative test of the disinfecting agent of example 3.

While the invention has been illustrated and described as embodied in a disinfection agent with parasiticidal action, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A disinfectant composition for killing invasive durable forms of parasites including oocysts of ascarides and coccidia, said composition consisting of water and a disinfection agent concentrate, wherein said disinfection agent concentrate consists of from 25 to 50% by weight of an active disinfectant ingredient consisting of at least one phenol combined with at least one keratolytically acting organic acid in a weight ratio of said at least one keratolytically acting organic acid to said at least one phenol between 1:9 and 9:1, said at least one keratolytically acting organic acid being selected from the group consisting of formic acid, salicylic acid and thioglycolic acid:

from 15 to 60% by weight of at least one solvent ingredient selected from the group consisting of ethylene glycol dialkyl ether compounds of the formula $H_3CO(CH_2-CH_2-O)_nCH_3$ with n =1 to 8; and from 5 to 30% by weight of at least one anionic surfactant ingredient selected from the group consisting of n-alkyl-aryl sulfonates having n-alkyl groups with from 10 to 13 carbon atoms sodium alkyl sulfonates, potassium salts of said n-alkyl-aryl sulfonates, sodium salts of said n-alkyl-aryl sulfonates, potassium alkyl sulfonates, sodium alkyl sulfonates, sodium alkyl sulfates and potassium alkyl sulfates, wherein said alkyl groups of said sodium and potassium alkyl sulfonates and said sodium and potassium alkyl sulfates have, independently, primary or secondary chains of from 8 to 18 carbon atoms.

2. The disinfectant composition as defined in claim 1, wherein said at least one phenol consists of 4-chloro-3-methylphenol.

3. The disinfecting composition as defined in claim 1 and containing from 0.5 to 10 percent by weight of said disinfection agent concentrate.

4. A disinfectant composition for killing invasive durable forms of parasites including oocysts of ascarides and coccidia, said composition consisting of water and a disinfection agent concentrate, wherein said disinfection agent concentrate consists of:

from 25 to 50% by weight of an active disinfectant ingredient consisting of at least one phenol combined with at least one keratolytically acting organic acid in a weight ratio of said at least one keratolytically acting organic acid to said at least one phenol between 1:9 and 9:1, said at least one keratolytically acting organic acid being selected from the group consisting of formic acid, salicylic acid and thioglycolic acid;

from 15 to 60% by weight of at least one solvent ingredient selected from the group consisting of ethylene glycol dialkyl ether compounds of the formula $H_3CO(CH_2-CH_2-O)_nCH_3$ with n =1 to 8;

from 0.2 to 2% by weight of a nonionic surfactant consisting of nonylphenol polyglycol ether ethoxylated with from 2 to 18 Mol of ethylene oxide; and from 5 to 30% by weight of at least one anionic surfactant ingredient selected from the group consisting of n-alkyl-aryl sulfonates having n-alkyl groups with from 10 to 13 carbon atoms sodium alkyl sulfonates, potassium salts of said n-alkyl-aryl sulfonates, sodium salts of said n-alkyl-aryl sulfonates, potassium alkyl sulfonates, sodium alkyl sulfonates, sodium alkyl sulfates and potassium alkyl sulfates, wherein said alkyl groups of said sodium and potassium alkyl sulfonates and said sodium and potassium alkyl sulfates have, independently, primary or secondary chains of from 8 to 18 carbon atoms.

5. The disinfectant composition as defined in claim 4, wherein said at least one phenol consists of 4-chloro-3-methylphenol.

6. The disinfecting composition as defined in claim 4 and containing from 0.5 to 10 percent by weight of said disinfection agent concentrate.

7. A disinfectant composition for killing invasive durable forms of parasites including oocysts of ascarides and coccidia, said composition consisting of water and a disinfection agent concentrate, wherein said disinfection agent concentrate consists of:

from 25 to 50% by weight of an active disinfectant ingredient consisting of at least one phenol combined with at least one keratolytically acting organic acid in a weight ratio of said at least one keratolytically acting organic acid to said at least one phenol between 1:9 and 9:1, said at least one keratolytically acting organic acid being selected from the group consisting of formic acid, salicylic acid and thioglycolic acid;

from 15 to 60% by weight of at least one solvent ingredient selected from the group consisting of alcohols having from 2 to 4 carbon atoms, ethylene glycol, propylene glycol and ethylene glycol dialkyl ethers of the formula $H_3CO(CH_2-CH_2-O)_nCH_3$ with n=1 to 8: and from 5 to 30% by weight of at least one anionic surfactant ingredient selected from the group consisting of n-alkyl-aryl sulfonates having n-alkyl groups with from 10 to 13 carbon atoms sodium alkyl sulfonates, potassium salts of said n-alkyl-aryl sulfonates, sodium salts of said n-alkyl-aryl sulfonates, potassium alkyl sulfonates, sodium alkyl sulfonates, sodium alkyl sulfates and potassium alkyl sulfates, wherein said alkyl groups of said sodium and potassium alkyl sulfonates and said sodium and potassium alkyl sulfates have, independently, primary or secondary chains of from 8 to 18 carbon atoms.

8. The disinfectant composition as defined in claim 7, wherein said at least one phenol consists of 4-chloro-3-methylphenol.

9. The disinfecting composition as defined in claim 7 and containing from 0.5 to 10 percent by weight of said disinfection agent concentrate.

10. The disinfectant composition as defined in claim 9, wherein said at least one solvent ingredient contains from 10 to 50% by weight of said ethylene glycol based on a total weight of said at least one solvent ingredient.

11. A method of killing invasive durable forms of parasites, including oocysts of ascarides and coccidia, said method consisting of the step of disinfecting with an effective amount of a disinfectant composition, said disinfectant composition consisting of water and a disinfection agent concentrate, wherein said disinfection agent concentrate consists of from 25 to 50% by weight of an active disinfectant ingredient consisting of at least one phenol combined with at least one keratolytically acting organic acid in a weight ratio of said at least one keratolytically acting organic acid to said at least one phenol between 1:9 and 9:1, said at least one keratolytically acting organic acid being selected from the group consisting of formic acid, salicylic acid and thioglycolic acid; from 15 to 60% by weight of at least one solvent ingredient selected from the group consisting of alcohols having from 2 to 4 carbon atoms, ethylene glycol, propylene glycol and ethylene glycol dialkyl ethers of the formula $H_3CO(CH_2-CH_2-O)_nCH_3$ with n=1 to 8; and from 5 to 30% by weight of at least one anionic surfactant ingredient selected from the group consisting of n-alkyl-aryl sulfonates having n-alkyl groups with from 10 to 13 carbon atoms sodium alkyl sulfonates, potassium salts of said n-alkyl-aryl sulfonates, sodium salts of said n-alkyl-aryl sulfonates, potassium alkyl sulfonates, sodium alkyl sulfonates, sodium alkyl sulfates and potassium alkyl sulfates, wherein said alkyl groups of said sodium and potassium alkyl sulfonates and said sodium and potassium alkyl sulfates have, independently, primary or secondary chains of from 8 to 18 carbon atoms.

12. The method as defined in claim 11, wherein said at least one phenol consists of 4-chloro-3-methylphenol.

13. The method as defined in claim 11, wherein said disinfectant composition contains from 0.5 to 10 percent by weight of said disinfection agent concentrate.

14. The method as defined in claim 11, wherein said at least one solvent ingredient contains from 10 to 50% by weight of said ethylene glycol based on a total weight of said at least one solvent ingredient.

15. A method of killing invasive durable forms of parasites, including oocysts of ascarides and coccidia, said method consisting of the step of disinfecting with an effective amount of a disinfectant composition, said disinfectant composition consisting of water and a disinfection agent concentrate, wherein said disinfection agent concentrate consists of from 25 to 50% by weight of an active disinfectant ingredient consisting of at least one phenol combined with at least one keratolytically acting organic acid in a weight ratio of said at least one keratolytically acting organic acid to said at least one phenol between 1:9 and 9:1, said at least one keratolytically acting organic acid being selected from the group consisting of formic acid, salicylic acid and thioglycolic acid; from 15 to 60% by weight of at least one solvent ingredient selected from the group consisting of ethylene glycol dialkyl ether compounds of the formula $H_3CO(CH_2-CH_2-O)_nCH_3$ with n=1 to 8; from 0.2 to 2% by weight of a nonionic surfactant consisting of nonylphenol polyglycol ether ethoxylated with from 2 to 18 Mol of ethylene oxide; and from 5 to 30% by weight of at least one anionic surfactant ingredient selected from the group consisting of n-alkyl-aryl sulfonates having n-alkyl groups with from 10 to 13 carbon atoms sodium alkyl sulfonates, potassium salts of said n-alkyl-aryl sulfonates, sodium salts of said n-alkyl-aryl sulfonates, potassium alkyl sulfonates, sodium alkyl sulfonates, sodium alkyl sulfates and potassium alkyl sulfates, wherein said alkyl groups of said sodium and potassium alkyl sulfonates and said sodium and potassium alkyl sulfates have, independently, primary or secondary chains of from 8 to 18 carbon atoms.

16. The method as defined in claim 15, wherein said at least one phenol consists of 4-chloro-3-methylphenol.

17. The method as defined in claim 15, wherein said disinfectant composition contains from 0.5 to 10 percent by weight of said disinfection agent concentrate.

18. A method of killing invasive durable forms of parasites including oocysts of ascarides and coccidia, infecting an area in which an animal is kept, said method consisting of the step of disinfecting said area in which said animal is kept with an effective amount of a disinfectant composition, said disinfectant composition consisting of water and a disinfection agent concentrate, wherein said disinfection agent concentrate consists of from 25 to 50% by weight of an active disinfectant ingredient consisting of at least one phenol combined with at least one keratolytically acting organic acid in a weight ratio of said at least one keratolytically acting organic acid to said at least one phenol between 1:9 and 9:1, said at least one keratolytically acting organic acid being selected from the group consisting of formic acid, salicylic acid and thioglycolic acid;

from 15 to 60% by weight of at least one solvent ingredient selected from the group consisting of ethylene glycol dialkyl ether compounds of the formula $H_3CO(CH_2-CH_2-O)_nCH_3$ with n=1 to 8; and from 5 to 30% by weight of at least one anionic surfactant ingredient selected from the group consisting of n-alkyl-aryl sulfonates having n-alkyl groups with from 10 to 13 carbon atoms sodium alkyl sulfonates, potassium salts of said n-alkyl-aryl sulfonates, sodium salts of said n-alkyl-aryl sulfonates, potassium alkyl sulfonates, sodium alkyl sulfonates, sodium alkyl sulfates and potassium alkyl sulfates, wherein said alkyl groups of said sodium and potassium alkyl sulfonates and said sodium and potassium alkyl sulfates have, independently, primary or secondary chains of from 8 to 18 carbon atoms.

19. The method as defined in claim 18, wherein said disinfectant composition contains from 0.5 to 10 percent by weight of said disinfection agent concentrate.

* * * * *